United States Patent

Bolz

(10) Patent No.: US 6,867,605 B2
(45) Date of Patent: Mar. 15, 2005

(54) CIRCUIT FOR DETERMINING THE INTERNAL RESISTANCE OF A LINEAR LAMBDA PROBE

(75) Inventor: Stephan Bolz, Pfatter (DE)

(73) Assignee: Siemens Aktiengesellschaft, Munich (DE)

( * ) Notice: Subject to any disclaimer, the term of this patent is extended or adjusted under 35 U.S.C. 154(b) by 60 days.

(21) Appl. No.: 10/341,564

(22) Filed: Jan. 13, 2003

(65) Prior Publication Data

US 2003/0151416 A1 Aug. 14, 2003

Related U.S. Application Data

(63) Continuation-in-part of application No. PCT/DE01/02575, filed on Jul. 10, 2001.

(30) Foreign Application Priority Data

Jul. 13, 2000 (DE) .......................................... 100 34 060
May 7, 2001 (DE) .......................................... 101 22 089

(51) Int. Cl.⁷ .......................... G01R 27/08; G01D 1/13
(52) U.S. Cl. ..................... 324/721; 324/713; 324/76.13
(58) Field of Search ................................. 324/721, 693, 324/713, 685, 76.13, 71.1; 73/1.06; 204/401, 425, 431

(56) References Cited

U.S. PATENT DOCUMENTS 4,419,190 A * 12/1983 Dietz et al. .................. 205/785
5,091,698 A * 2/1992 Grabs .......................... 324/693
5,777,468 A * 7/1998 Maher .................... 324/207.18
5,914,593 A * 6/1999 Arms et al. ............. 324/207.12
2001/0037683 A1 * 11/2001 Nozoe et al. ............. 73/504.16

FOREIGN PATENT DOCUMENTS

| DE | 3117790 A1 | 11/1982 | ............ G01K/7/26 |
| DE | 31717 790 A1 | 11/1982 | ............ G01K/7/26 |
| DE | 3836045 A1 | 4/1990 | ............ G01R/27/16 |
| DE | 3903314 A1 | 9/1990 | ............ G01R/27/14 |
| DE | 19636226 A1 | 12/1998 | ............ F02D/41/14 |
| EP | 0 478 813 A1 | 4/1992 | ............ G01D/5/22 |
| WO | 01/96848 A1 | 12/2001 | ......... G01N/27/406 |

* cited by examiner

Primary Examiner—Anjan K. Deb
(74) Attorney, Agent, or Firm—Baker Botts L.L.P.

(57) ABSTRACT

A device for measuring the probe impedance of a linear lambda probe of an internal combustion engine which is caused by an AC current measurement signal which is fed into the lambda probe, comprises a voltage amplifier for amplifying an AC voltage which drops across the probe impedance, and a rectifier for rectifying the amplified AC voltage, wherein the rectifier is a synchronous demodulator, by which in each case the upper and lower amplitude of the AC voltage signal is sampled with its frequency, filtered and stored, and by which the difference of the stored signals is amplified with a gain factor and made available as output signal at its output for controlling the temperature of the lambda probe.

16 Claims, 4 Drawing Sheets

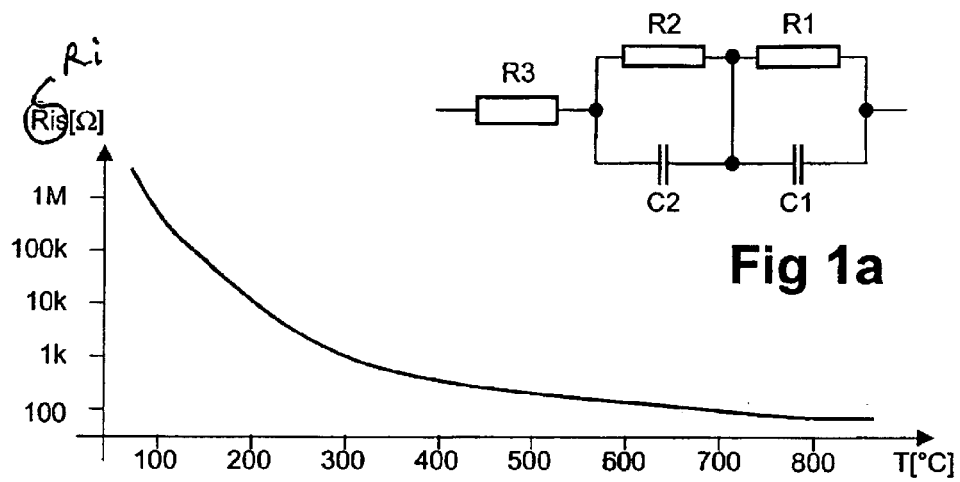
Fig 1a
Fig 1b
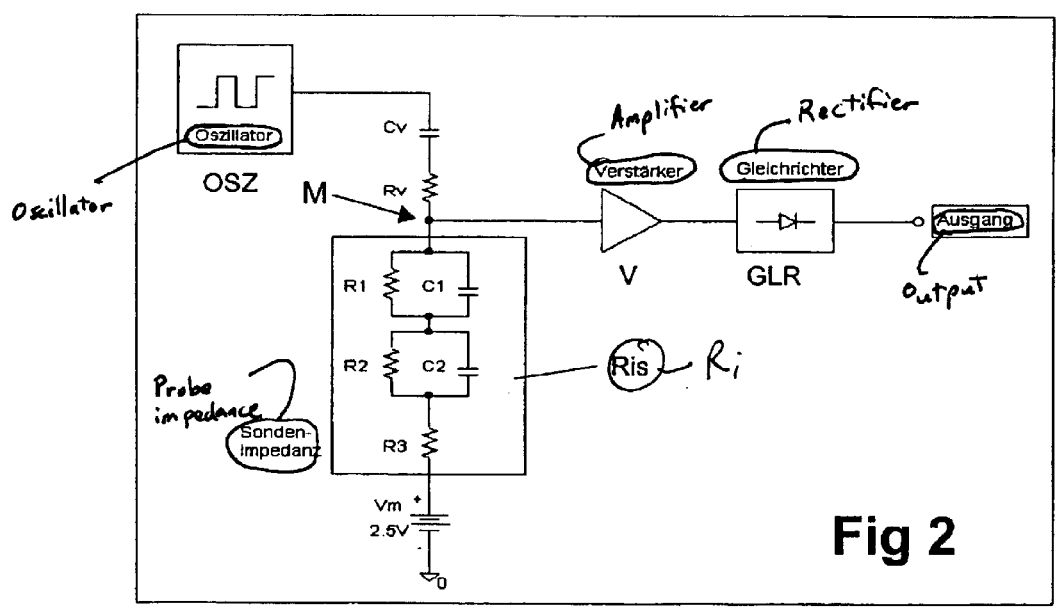
Fig 2

CIRCUIT FOR DETERMINING THE INTERNAL RESISTANCE OF A LINEAR LAMBDA PROBE

CROSS REFERENCE TO RELATED APPLICATION

This application is a continuation-in-part of copending International Application No. PCT/DE01/02575 filed Jul. 10, 2001, which designates the United States, and claims priority to German application number 10034060.1 filed Jul. 13, 2000 and German application number 10122089.8 filed May 7, 2001.

BACKGROUND OF THE INVENTION

The invention relates to a circuit for determining the internal resistance of a linear lambda probe.

The transmission function of a linear lambda probe has a high degree of dependence on temperature, which has to be compensated by controlling the probe temperature. However, for reasons of cost the probe temperature is not measured by means of a separate sensor (for example Pt100) but instead the high temperature dependence of the probe impedance Ri is utilized. FIGS. 1a and 1b show the temperature dependence and equivalent circuit of the probe impedance. Here, R1/C1 represents the contact resistance between electrodes and ceramic material, R2/C2 represents the junction between the grain boundaries of the sintered ceramic grains, and R3 represents the intrinsic resistance of the sintered material.

R1 is highly subject to ageing and therefore cannot be used for measuring temperature. Given a suitable selection of the measurement frequency—for example 3 kHz—R1 is short-circuited in terms of AC voltage by means of C1; it therefore makes no contribution to the overall impedance any more. The series connection of R2/C2 and R1 yields an absolute value of 100 ohms with this measuring frequency at approximately 500° C. and can be used for determining the temperature.

The older patent application 2000 P 12334 DE (official file number not yet known) which was not published before the priority date describes a customary measurement method for determining the probe impedance Ri. According to said method, a square-wave AC current, for example 500 µAss (peak-to-peak), is applied to the probe impedance.

An AC voltage of 500 µAss*100 ohm=50 mVss is produced at Ri. This AC voltage is amplified and rectified and can then be fed to a microprocessor for controlling the temperature.

The AC current is generated according to FIG. 2, for example, by means of a 3 kHz square-wave oscillator which is supplied with 5 V. The signal is conducted to the probe impedance via a high impedance resistor Rv and a decoupling capacitor Cv.

SUMMARY OF THE INVENTION

The object of the invention is to improve the measurement of the impedance (of the internal resistance) Ri of a linear lambda probe and to reduce the error in the rectification of the AC voltage signal, and to reduce the sensitivity to electromagnetic interference pulses (EMC). In general terms, the object of the invention is to acquire precisely the peak-to-peak amplitude value (Vss) of an AC voltage signal whose phase is known and on which a DC voltage is superimposed.

This object can be achieved by a device for measuring the probe impedance of a linear lambda probe of an internal combustion engine which is caused by an AC current measurement signal which is fed into the lambda probe, having a voltage amplifier for amplifying an AC voltage which drops across the probe impedance, and having a rectifier for rectifying the amplified AC voltage, wherein the rectifier is a synchronous demodulator, by which in each case the upper and lower amplitude of the AC voltage signal is sampled with its frequency, filtered and stored, and by which the difference of the stored signals is amplified with a gain factor and made available as output signal at its output for controlling the temperature of the lambda probe.

An oscillator can be provided from whose output signal both the AC current measurement signal and the control signals for the synchronous demodulator are acquired. The synchronous demodulator may comprise a first sample and hold circuit in which the upper amplitude of the input signal is sampled and held, a second sample and hold circuit in which the lower amplitude of the input signal is sampled and held, a decoupling amplifier connected downstream of each sample and hold circuit, and a differential amplifier which forms a differential signal from the output signals of the two decoupling amplifiers and makes available as output signal at the output of the synchronous demodulator as control signal for controlling the temperature of the lambda probe. The resistor and the capacitor of each sample and hold circuit may form, in the sampling phase, a low-pass filter for the integrated averaging of the input signal, and the capacitors may act as holding capacitors in the hold phase. Each of the two capacitors can be placed at a predefined potential. Both of the decoupling amplifiers can have a predefined gain factor. A resistor can be arranged between the output of each of the two decoupling amplifiers and the assigned input of the differential amplifier, and both resistors may have the same resistance value. A voltage divider may lead from the noninverting input of the differential amplifier to a reference potential, and a resistor can be arranged between the tap of the voltage divider and a predefined potential. The resistance value of the series connection of the resistors can be equal to that of a resistor which is arranged between the output and inverting input of the differential amplifier. By actuating the switches with control signals, the synchronous demodulator may sample in each case only a portion which is less than 50% of the period of the AC voltage signal with its frequency.

A method for measuring the probe impedance of a linear lambda probe of an internal combustion engine, may comprise the steps of:
  feeding an AC current measurement signal into the lambda probe;
  amplifying an AC voltage which drops across the probe impedance, and
  rectifying the amplified AC voltage by means of a synchronous demodulator, by which in each case the upper and lower amplitude of the AC voltage signal is sampled with its frequency, filtered and stored, and by which the difference of the stored signals is amplified with a gain factor and made available as output signal at its output for controlling the temperature of the lambda probe.

The method may further comprise the step of generating an oscillator signal from which both the AC current measurement signal and the control signals for the synchronous demodulator are acquired. The method may further comprise the steps of:
  sampling and holding the upper amplitude of the input signal;

sampling and holding the lower amplitude of the input signal;

decoupling the sampled and held signals, and forming a differential signal from the decoupled signals and making it available as an output signal at the output of the synchronous demodulator as a control signal for controlling the temperature of the lambda probe. The method can further comprise the step of providing, in the sampling phase, a low-pass filter for the integrated averaging of the input signal. The decoupling can be performed with a predefined gain factor. The step of sampling and holding can be performed in such a way that in each case only a portion which is less than 50% of the period of the AC voltage signal with its frequency is sampled.

BRIEF DESCRIPTION OF THE DRAWINGS

FIGS. 1a and 1b show the temperature dependence and equivalent circuit of the probe impedance, FIG. 2 shows the circuit of a device for measuring the probe impedance.

DETAILED DESCRIPTION OF THE PREFERRED EMBODIMENTS

Figure 3:
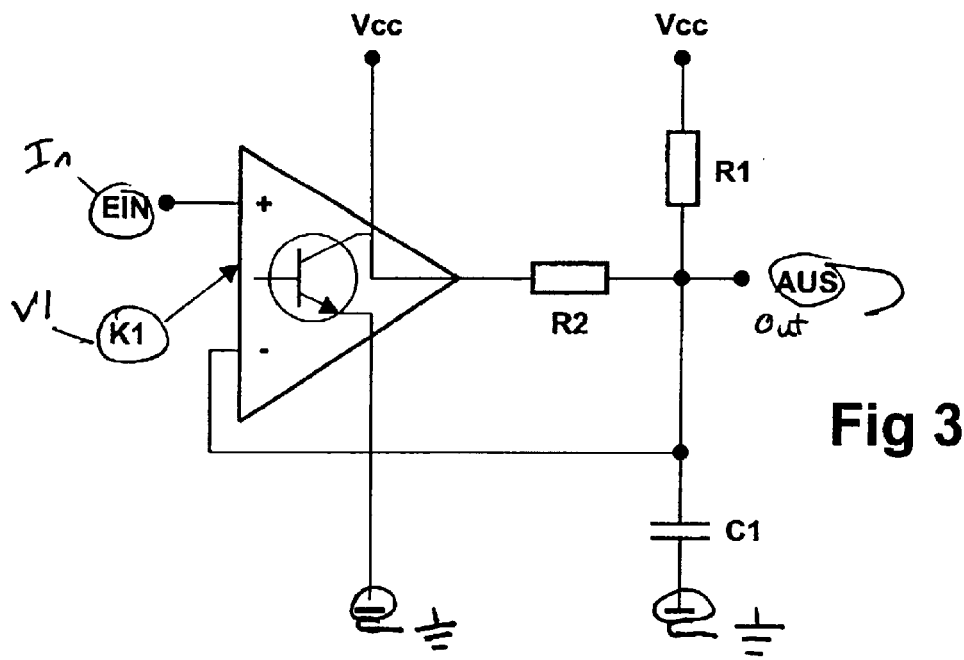
FIG. 3 shows a peak value rectifier.

In the known circuit, a peak value rectifier (illustrated in FIG. 3) is used to convert the AC voltage signal into a DC voltage. Said rectifier operates as follows: it will be assumed that there is a DC voltage of 2.5 V (center voltage Vm) at the input. The comparator V1 operates as a voltage follower; the voltage at the output is therefore also 2.5 V. This is achieved in that C1 charges slowly via R1. As long as the voltage at the output is lower than the input voltage, the output transistor of the comparator V1 remains switched off. If the output voltage exceeds the input voltage, the transistor switches on and discharges C1 via R2 until the output voltage is below the input voltage again. The transistor then switches off again and the output voltage rises slowly again, driven by the charge current of R1.

Oscillation occurs about Vout=Vm. The important factor here is that the time constants for the charging and discharging of the capacitor are very different:

$$\tau charge = R1*C1, \tau discharge = R2*C1$$

In a real circuit, the ratio τcharge/τdischarge of approximately 100/1 is selected, which results in a measuring error of 1%. If, for example, a square-wave signal with 500 mVss amplitude and with a DC voltage of Vm (2.5 V) superimposed on it is applied to the input, of the output will very quickly follow the lower peak value of the input signal (negative half wave) and rise only slowly again at the upper peak value. In the method of operation, a DC voltage which corresponds to the lower peak value of the input (AC+DC) voltage is thus produced at the output, see FIG. 4.

Figure 4:
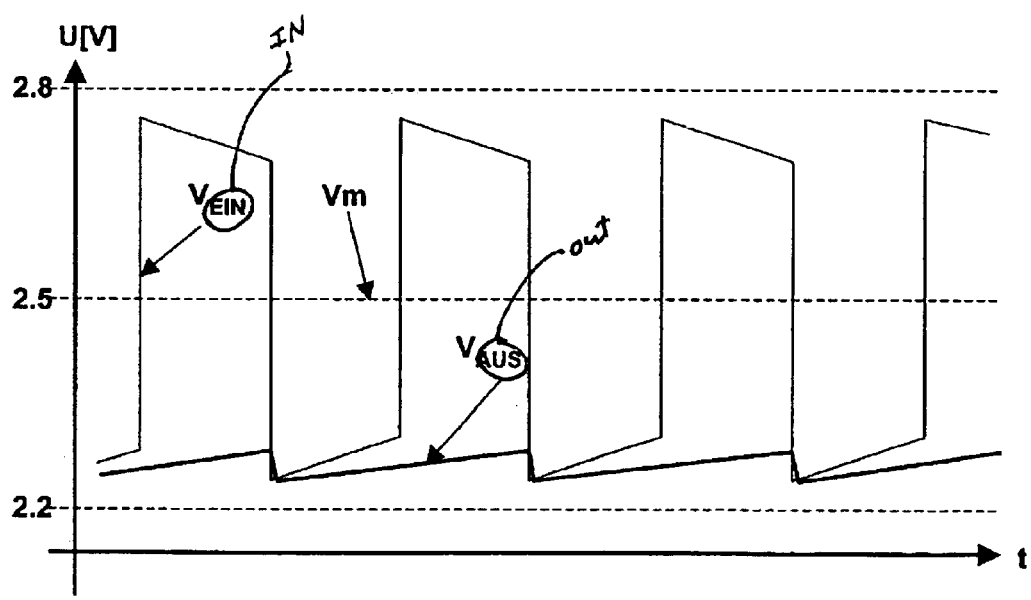
FIG. 4 shows a DC voltage which corresponds to the lower peak value of the input (AC+DC) voltage.

The rectifier converts the AC voltage signal (500 mVss)—upper curve in FIG. 4—into a DC voltage signal (−250 mV)—lower curve. The zero point is at Vm=+2.5 V. The output signal is therefore on average

+2.50 V−0.25 V=+2.25 V.

The filter time constant has been greatly reduced in order to clarify the method of operation. The output signal therefore shows increased ripple in comparison to the typical application. This results in a simple, cost-effective design which uses standard components and fulfils the original precision requirements.

However, this circuit gives rise to a falsification of the output value when there is a pulse tilt of the square-wave signal (for example owing to excessively small coupling capacitors or effects of the probe control loop) and it has a high degree of sensitivity to EMC interference pulses, due to the rapid response of the rectifier.

According to the invention, the peak value rectifier is replaced by a synchronous demodulator with integrated filtering means. As the phase and frequency of the measurement signal are known, it is possible to perform rectification controlled by the oscillator signal.

Figure 5:
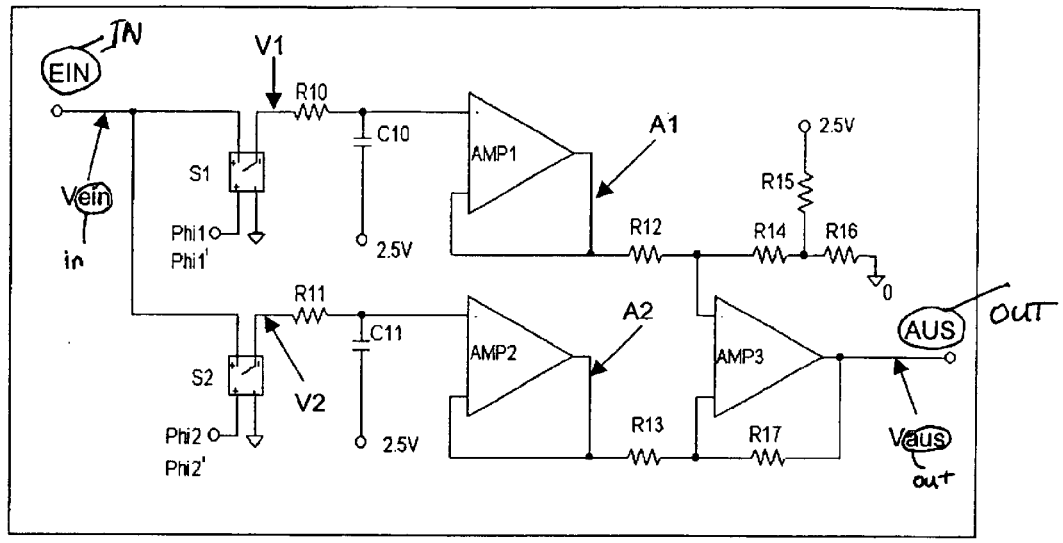
FIG. 5 shows the circuit of a synchronous demodulator according to the invention with integrated filtering means.

FIG. 5 shows the circuit of a synchronous demodulator according to the invention with integrated filtering means.

The input of the circuit is connected to the output of the amplifier shown in FIG. 2 and to the inputs of the switches S1, S2. The output of S1 is connected to a terminal of the capacitor C10 via resistor R10 and to the noninverting input of the amplifier AMP1. The other terminal of C10 is connected to the DC voltage source Vm (2.5 V) shown in figure 2. The inverting input of AMP1 is connected to its output.

The output of S2 is connected to a terminal of the capacitor C11 via resistor R11 and to the noninverting input of the amplifier AMP2. The other terminal of C11 is connected to Vm. The inverting input of AMP2 is connected to its output.

The resistor R12 is connected on the one hand to the output of AMP1 and on the other hand to the noninverting input of AMP3 and R14. The other terminal of R14 is connected to R15 and R16. The other terminal of R15 is connected to 2.5 V, and that of R16 to ground. R13 is connected on the one hand to the output of AMP2, and on the other hand to the inverting input of AMP3 and R17. R17 is also connected to the output of AMP3 where the output of the circuit is located.

S1, R10 and C10 constitute a sample and hold circuit, as do S2, R11 and C11. Phi1 is the control signal of the switch S1, it corresponds for example to the signal of the oscillator shown in FIG. 2. S1 is closed as long as the oscillator signal is 5 V, and open if the oscillator signal is 0 V.

In this way, the capacitor C10 is connected to the input via R11 during the positive phase of the oscillator signal. Said capacitor will consequently slowly charge to the positive value of the input signal—in accordance with the time constant τ=R10*C10. Averaging to the positive signal value is carried out by synchronizing the switch activation and input signal. C10 is not connected to ground but rather to Vm=2.5 V. As a result, the DC voltage present at the capacitor C10 is reduced, which reduces the leakage current of the capacitor.

The downstream amplifier AMP1 has a gain 1 and is used for the high impedance decoupling of C10 in order to avoid discharging in the hold phase (S1 open). At the output of AMP1 a DC voltage is produced which corresponds to the DC voltage Vm=+2.5 V and the positive peak value of the input signal. Vout (AMP1)=0.025 V+2.5 V=+2.525 V.

The second sample and hold circuit (S2, R11, C11) is used to measure the negative signal value. The control signal Phi2 is therefore inverted with respect to S1. The rest of the behavior corresponds otherwise to the first sample and hold circuit, the voltage −0.025 V+2.5 V=2.475 V then being produced at the output of AMP2.

The amplifier AMP3 forms a differential amplifier together with the resistors R12, R13, R14, R15, R16, R17). R12 and R13 have the same resistance value. The resistance of the series connection of R14 with the parallel connection of R15 and R16 corresponds here to that of R17. The gain factor is determined by means of the ratio of R17 and R13 (Vu=R17/R13). A further voltage (+2.5 V) is fed to the differential amplifier AMP3 via R15. Given an appropriate selection of R14, R15 and R16, a specific output voltage can thus be defined when there is no input voltage. This offset is necessary, like the DC voltage Vm=+2.5 V, for systems with no negative supply voltage as it is then impossible for the output of the amplifier AMP3 to reach 0 V. Operation of the circuit in a 0/5 V power system is made possible only by Vm and the offset.

The differential amplifier which is produced in this way then converts the difference between the output voltages of AMP1 and AMP2 into an output signal, the DC voltage (2.5 V) which is common to the input signals being suppressed and the difference being amplified by the value of the gain Vu.

A rectified representation of the input signal which is amplified by Vu and which is still shifted by the offset is produced at the output of AMP3. This voltage can then be fed, for example, to the A/D converter of a microcontroller for further digital processing.

In order to increase the precision of the synchronous rectifier further, it is possible to change the switch-on times of S1 and S2 as a function of the shape of the curve of the input signal.

If the input signal has, for example, an exponential pulse tilt, it is appropriate to measure only the rear part of the positive or negative amplitude. To do this, a further circuit is necessary which generates further signals with a changed phase angle and pulse width (modified Phi1 and Phi2) from the oscillator signal. Phi1 will in this case no longer be assumed to be 0% to 50% of the oscillator signal of 5 V but rather only 25% to 50% of said signal. Phi2 in this case will no longer be assumed to be 50% to 100% but rather only 75% to 100%.

Correspondingly, only the range of 25% to 50% of the positive amplitude value of the input signal will now be sampled in the first sample and hold circuit, and the range of 75% to 100% of the negative amplitude value will be sampled.

Figure 6:
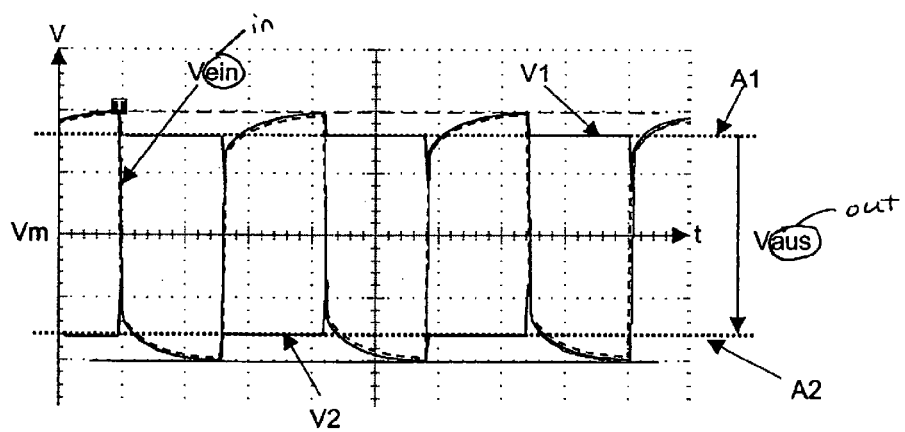
FIG. 6 shows the input signal and the signal downstream of the switches S1 and S2.

FIG. 6 shows the input signal and the signal downstream of the switches S1 and S2.

The upper trace (moved upward for better visibility) shows the signal at the output of S1. As long as S1 is closed, it follows the curve profile of the input signal (e-function), and when S1 is open the voltage is visible at C10 (straight line).

The central trace represents a—real—input signal as formed by the complex internal resistance of the linear lambda probe.

The lower trace (moved downward for better visibility) shows the signal at the output of S2.

Figure 7:
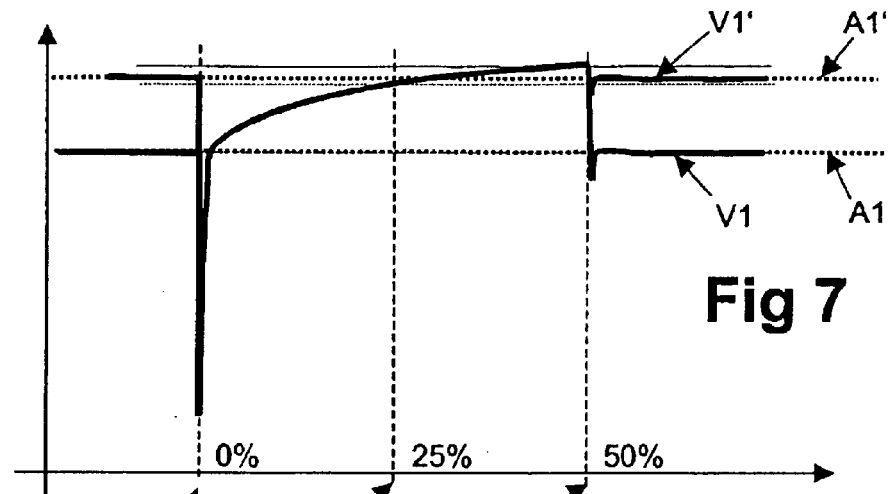
FIG. 7 shows a detailed portion of the upper trace of FIG. 6.

FIG. 7 shows a detailed portion of the upper trace of FIG. 6:
 unbroken line: peak value of the signal,
 vertical center of diagram: voltage at C10,
 horizontal center of diagram: 25% point of the signal,
 dashed line: new averaging interval.

The measurement error of the synchronous demodulator is 14 mV or 7% referred to the signal amplitude of 200 mVss used here. The reason for this is the extremely high fluctuation of the positive amplitude value over which averaging is carried out (exponential function).

When a sampling interval of 25% to 50% is used, this fluctuation is reduced to approximately 7 mV (difference between unbroken and dashed lines in FIG. 7) so that after the averaging a residual error of <3 mV is obtained, which corresponds to 1.5%.

Figure 9:
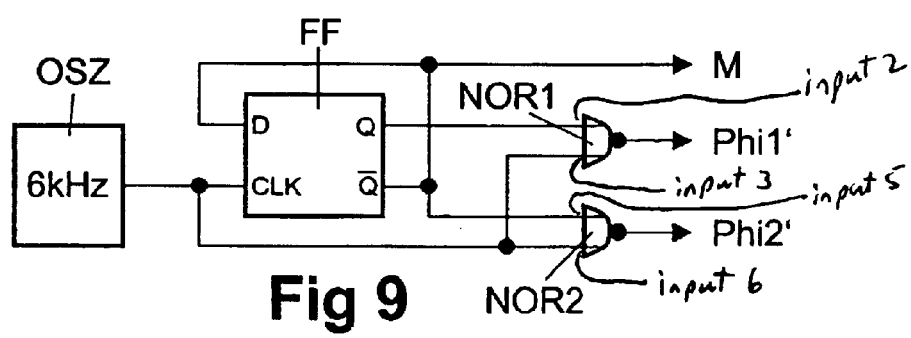
FIG. 9 shows a circuit for generating the phase-shifted signals Phi1' and Phi2'.

FIG. 9 shows a circuit for generating the phase-shifted signals Phi1' and Phi2' and of the 3 kHz signal M.

The output of the oscillator OSZ is connected to the clock input CLK of the flip-flop IC1A FF and to the input 3 of the NOR gate IC2A NOR1, and to the input 6 of the NOR gate IC2B NOR1. The output Q of the flip-flop IC1A FF is connected to the input 2 of the gate IC2A NOR1. The output Q transverse of the flip-flop IC1A FF is connected to its data input D and to the input 5 of the gate IC2B NOR2; it constitutes the 3 kHz signal M. The output of the gate IC2A NOR1 constitutes the signal Phi1', and the output of the gate IC2B NOR2 constitutes the signal Phi2'.

Owing to the feeding back of the output Q transverse, the flip-flop IC1A FF operates on the data input as a frequency divider (:2). The 3 kHz signal M, which is conducted to the probe impedance Ri via Rv and Cv (FIG. 2), is correspondingly produced at the output Q transverse. IC1 switches with the rising edge of the 6 kHz oscillator. The oscillator signal is fed, together with the output signal Q transverse (of IC1A FF), to the inputs of the gate IC2B NOR2. If both input signals are 0 V, its output is 5 V. Referred to the 3 kHz signal M this is the case from 75% to 100% of the clock phase, as required above for Phi2'.

The oscillator signal is then also fed, together with the output signal Q (of Id1A), to the inputs of the gate IC2A NOR1. If both input signals are 0 V, its output signal is 5 V. Referred to the 3 kHz signal M, this is the case from 25% to 50% of the clock phase, as required above for Phi1'.

Figure 8:
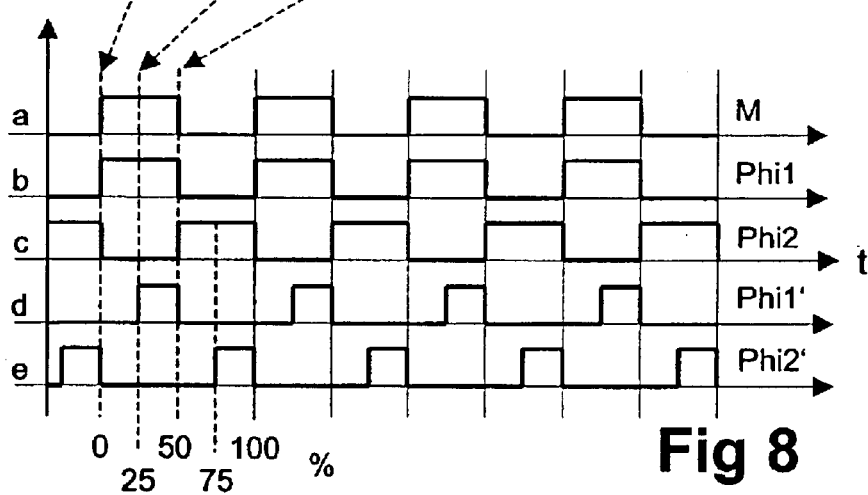
FIG. 8 shows a 3 kHz measurement signal and control signals in five signal profiles plotted against time being applied when there is a 50% and a 25% sampling interval, as illustrated in FIG. 7.

FIG. 8 shows 3 kHz measurement signal M and control signals Phi1, Phi2, Phi1' and Phi2' in five signal profiles plotted against time t, as illustrated in FIG. 7. The control signals Phi1 and Phi2, Phi1' and Phi2'b being applied when there is a 50% and a 25% sampling interval.

What is claimed is:

1. A device for measuring the probe impedance of a linear lambda probe of an internal combustion engine which is caused by an AC current measurement signal which is fed into the lambda probe, comprising
 a voltage amplifier for amplifying an AC voltage which drops across the probe impedance, and
 a rectifier for rectifying the amplified AC voltage, wherein the rectifier is a synchronous demodulator, by which in each case the upper and lower amplitude of the AC voltage signal is sampled with its frequency, filtered and stored, and by which the difference of the stored signals is amplified with a gain factor and made available as output signal at its output for controlling the temperature of the lambda probe.

2. The device as claimed in claim 1, wherein an oscillator is provided from whose output signal both the AC current measurement signal and the control signals for the synchronous demodulator are acquired.

3. The device as claimed in claim 1, wherein the synchronous demodulator has a first sample and hold circuit in which the upper amplitude of the input signal is sampled and held, and has a second sample and hold circuit in which the lower amplitude of the input signal is sampled and held, has a decoupling amplifier connected downstream of each sample and hold circuit, and has a differential amplifier which forms a differential signal from the output signals of the two decoupling amplifiers and makes available as output signal at the output of the synchronous demodulator as control signal for controlling the temperature of the lambda probe.

4. The device as claimed in claim 3, wherein the resistor and the capacitor of each sample and hold circuit form, in the sampling phase, a low-pass filter for the integrated averaging of the input signal, and wherein the capacitors act as holding capacitors in the hold phase.

5. The device as claimed in claim 3, wherein each of the two capacitors is placed at a predefined potential.

6. The device as claimed in claim 3, wherein both the decoupling amplifiers have a predefined gain factor.

7. The device as claimed in claim 3, wherein a resistor is arranged between the output of each of the two decoupling amplifiers and the assigned input of the differential amplifier, and both resistors have the same resistance value.

8. The device as claimed in claim 3, wherein a voltage divider leads from the noninverting input of the differential amplifier to a reference potential, and wherein a resistor is arranged between the tap of the voltage divider and a predefined potential.

9. The device as claimed in claim 8, wherein the resistance value of the series connection of the resistors is equal to that of a resistor which is arranged between the output and inverting input of the differential amplifier.

10. The device as claimed in claim 1, wherein, by actuating switches with control signals, the synchronous demodulator samples in each case only a portion which is less than 50% of the period of the AC voltage signal with its frequency.

11. A method for measuring the probe impedance of a linear lambda probe of an internal combustion engine, comprising the steps of:

feeding an AC current measurement signal into the lambda probe;

amplifying an AC voltage which drops across the probe impedance, and rectifying the amplified AC voltage by means of a synchronous demodulator, by which in each case the upper and lower amplitude of the AC voltage signal is sampled with its frequency, filtered and stored, and by which the difference of the stored signals is amplified with a gain factor and made available as output signal at its output for controlling the temperature of the lambda probe.

12. The method as claimed in claim 11, further comprising the step of generating an oscillator signal from which both the AC current measurement signal and the control signals for the synchronous demodulator are acquired.

13. The method as claimed in claim 11, further comprising the steps of:

sampling and holding the upper amplitude of the input signal;

sampling and holding the lower amplitude of the input signal;

decoupling the sampled and held signals, and forming a differential signal from the decoupled signals and making it available as an output signal at the output of the synchronous demodulator as a control signal for controlling the temperature of the lambda probe.

14. The method as claimed in claim 13, further comprising the step of providing, in the sampling phase, a low-pass filter for the integrated averaging of the input signal.

15. The method as claimed in claim 13, wherein the decoupling is performed with a predefined gain factor.

16. The method as claimed in claim 11, wherein the step of sampling and holding is performed in such a way that in each case only a portion which is less than 50% of the period of the AC voltage signal with its frequency is sampled.

* * * * *